(12) United States Patent
Kostadimas

(10) Patent No.: US 6,679,868 B2
(45) Date of Patent: Jan. 20, 2004

(54) SELF-SECURING SYSTEM FOR CATAMENIAL HYGIENE PRODUCTS

(76) Inventor: Olivia Kostadimas, 2237 1/2 N. Lincoln Ave. #2B, Chicago, IL (US) 60614

(*) Notice: Subject to any disclaimer, the term of this patent is extended or adjusted under 35 U.S.C. 154(b) by 0 days.

(21) Appl. No.: 09/873,595

(22) Filed: Jun. 4, 2001

(65) Prior Publication Data

US 2002/0183710 A1 Dec. 5, 2002

(51) Int. Cl.7 ............................................... A61F 13/15
(52) U.S. Cl. ................................. 604/385.18; 604/904
(58) Field of Search ................................. 604/358, 344, 604/351, 352, 346, 327, 385.03, 385.05, 385.17, 385.18, 386, 389, 390, 401, 904

(56) References Cited

U.S. PATENT DOCUMENTS

| | | |
|---|---|---|
| 3,037,506 A | 6/1962 | Penska |
| 3,948,257 A | 4/1976 | Bossak |
| 4,648,867 A | 3/1987 | Conner et al. |
| 6,017,321 A | 1/2000 | Boone |
| 6,312,419 B1 * | 11/2001 | Durel-Crain ........... 604/385.18 |

* cited by examiner

Primary Examiner—Jeanette Chapman
(74) Attorney, Agent, or Firm—Harness, Dickey & Pierce, P.L.C.

(57) ABSTRACT

A system and method for securing the removal element of a catamenial device, i.e. the withdrawal string of a tampon, to a surface, and more specifically to an undergarment or bathing suit, is provided. Generally, the withdrawal string is secured to a surface to prevent undesirable projection of the withdrawal string outside, for example, a bathing suit when the user is at a beach or pool. Further, the withdrawal string is secured to a surface during use of the tampon to prevent fluids from coating the withdrawal string, thereby improving sanitary use of a tampon. The system comprises an adhesive element that occurs along the removal element such that the removal element is secured when pressed against a surface. The adhesive element comprises at least one adhesive tab attached to a withdrawal string, and in another form an adhesive coating over at least a portion of a withdrawal string.

5 Claims, 9 Drawing Sheets

B – B

D - D

SELF-SECURING SYSTEM FOR CATAMENIAL HYGIENE PRODUCTS

FIELD OF THE INVENTION

The present invention relates generally to catamenial hygiene products and more particularly to systems and methods for securing the removal element of an absorbent member, such as the withdrawal string of a tampon, during use.

BACKGROUND OF THE INVENTION

With catamenial hygiene products of the known art, there is currently a lack of certain features to secure a withdrawal string of a tampon so as to prevent the string from inadvertently projecting outside the garment of a user, and to secure the withdrawal string away from fluids during use. For example, when a user is at the beach or swimming pool, it is advantageous for the withdrawal string to remain tucked inside the bathing suit so as to avoid any embarrassment should the string project, or hang, therefrom.

During use, it is also advantageous to position the withdrawal string away from the proximity of the tampon so that any overflow that cannot be absorbed by the tampon does not flow onto the withdrawal string. Typically, the user grasps the withdrawal string with a bare hand to remove the tampon, thus making removal unsanitary when the string is covered with overflow. Additionally, the withdrawal string should be positioned away from the proximity of the tampon during evacuation so that fluids (e.g., urine, endometrium, blood) similarly do not flow onto the withdrawal string.

Catamenial hygiene products of the known art have not provided a means for securing the removal element of absorbent members, i.e. the withdrawal string of a tampon, inside a garment of the user or away from fluids during use. Known art tampons have, however, used the withdrawal string to retain certain devices for other purposes. For example, U.S. Pat. No. 3,948,257 to Bossak discloses a deodorant system wherein a small tag having a deodorant is affixed to the withdrawal string. However, no means for securing the withdrawal string to a surface is disclosed or taught. Additionally, U.S. Pat. No. 6,017,321 to Boone discloses an adhesive sticker affixed to the withdrawal string to act as a reminder to the user so that the tampon is not in place for an excessive period of time. The adhesive sticker, however, does not secure the withdrawal string to a surface and only acts as a reminder to periodically change the tampon.

Accordingly, there remains a need in the art for a system that secures the removal element of an absorbent member, such as the withdrawal string of a tampon, to prevent projection of the element outside a garment, and further, to prevent fluids from coating the element during use, thereby improving the sanitary use of catamenial hygiene products.

SUMMARY OF THE INVENTION

Generally, the present invention provides an adhesive element that is secured to the removal portion of an absorbent member of catamenial hygiene products. The removal portion and absorbent member may be a withdrawal string and a tampon, a removal portion and a sanitary napkin, or other catamenial hygiene product having a removal portion.

In one preferred form, the present invention provides at least one adhesive tab that is attached to the withdrawal string of a tampon. The adhesive tab comprises at least one side having an adhesive layer that secures the string to a surface, i.e. an article of clothing, when the tab is pressed against the surface. Preferably, the adhesive tab is positioned near the free end of the withdrawal string, away from the absorbent insert of the tampon. Alternately, a plurality of adhesive tabs may be placed along the length of the withdrawal string for adequate securement as required. Moreover, the adhesive tab is attached to the withdrawal string using an adhesive, or by other methods commonly known in the art such as stitching.

The adhesive tab is either manufactured with the tampon assembly or may alternately be secured to existing withdrawal strings by the user. For existing withdrawal strings, an adhesive tab configuration is provided that comprises a double-sided adhesive member, which is wrapped around the withdrawal string such that one side of the adhesive member secures the tab to itself and the string, and the other side of the adhesive member secures the string to a surface. Accordingly, the adhesive tab of the present invention is easily retrofittable to withdrawal strings of existing tampons.

In another preferred form, the present invention provides an adhesive coating to at least a portion of the withdrawal string such that the string is secured when pressed against a surface. Preferably, the adhesive coating is applied to the free end of the withdrawal string, away from the absorbent insert of the tampon. Alternately, the adhesive coating is applied along the entire length of the withdrawal string for additional bonding strength. In yet another form, the adhesive coating is applied in alternating segments along the length of the withdrawal string according to the desired bonding strength and adhesive material utilized.

The adhesive layer or coating that is applied to the adhesive tab and the withdrawal string for securement to a surface generally has a low shear strength such that the withdrawal string is easily removed from the surface while providing adequate bond strength after repeated cycles of securement and removal as necessary during use. In addition to securement of the withdrawal string to a surface such as a garment, the user may also temporarily secure the withdrawal string to an area of their inner thigh during evacuation, and accordingly, the adhesive must be easily and comfortably removed therefrom.

In yet another preferred form, the present invention contemplates application of the adhesive element to a removal portion of sanitary napkins. The adhesive element is similarly an adhesive tab or coating that is applied to the removal portion, which may be a string or other like element, such that the removal portion is firmly secured to a surface.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiments is merely exemplary in nature and is in no way intended to limit the invention, its application, or uses.

Figure 1:
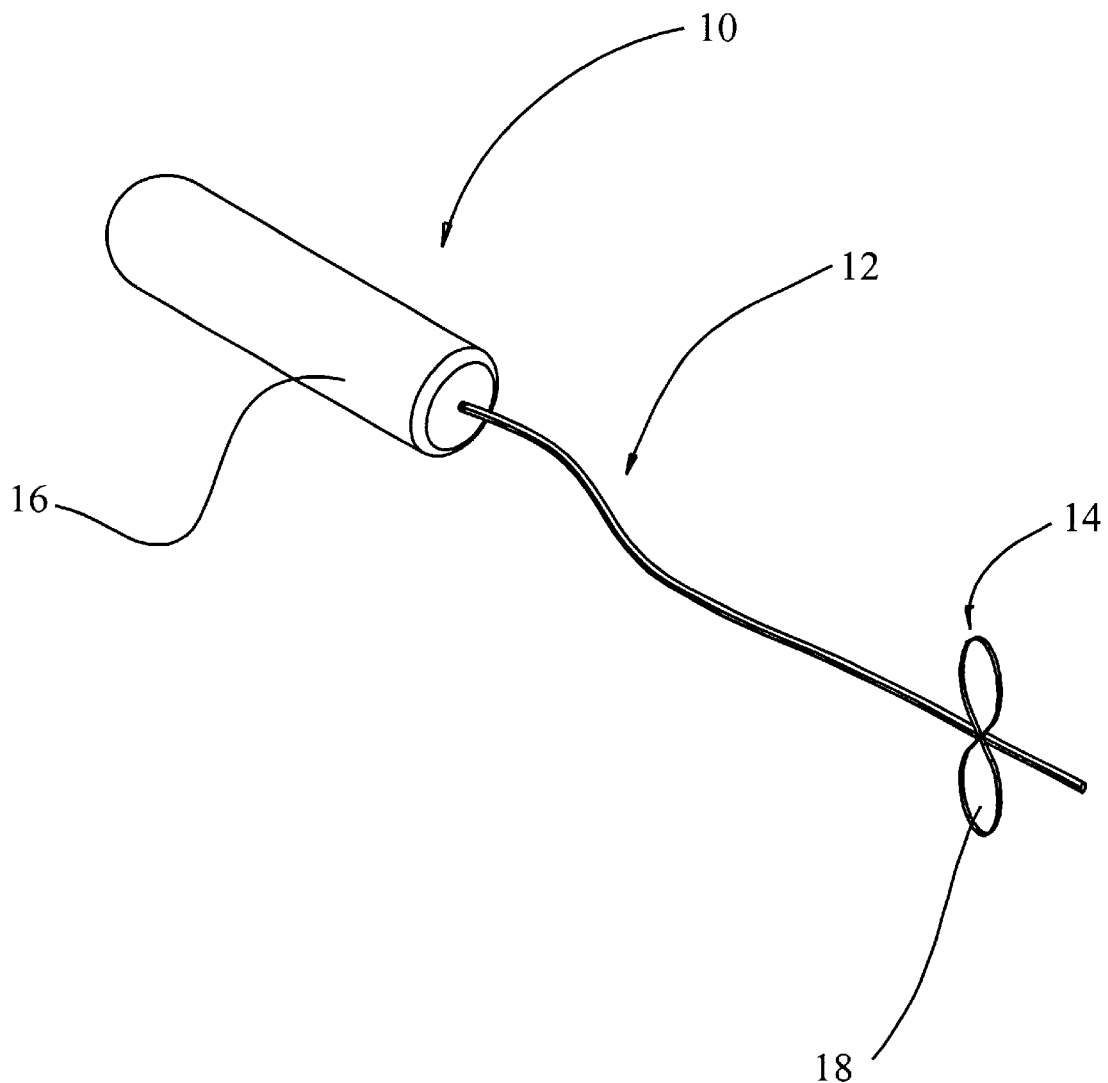
FIG. 1 is an orthogonal view of an adhesive tab attached to a withdrawal string in accordance with the present invention.

Referring to the drawings, a self-securing withdrawal string system of the present invention is illustrated and generally indicated by reference numeral 10 in FIG. 1. Generally, the self-securing withdrawal string system 10 comprises an adhesive tab 14 attached to a withdrawal string 12, wherein the withdrawal string 12 is attached to an absorbent member 16 of a tampon. Preferably, the adhesive tab 14 is attached to the withdrawal string 12 using an adhesive, although other methods commonly known in the art, such as stitching, could also be employed to attach the adhesive tab 14 to the withdrawal string 12.

The adhesive tab 14 further comprises at least one surface 18 that is coated with an adhesive material having a low shear strength. The low shear strength adhesive allows the adhesive tab 14 to be easily and repeatably secured to and removed from a surface with mild pressure and force from the hands or fingers of a user. As a result, the adhesive tab 14 can be repeatably secured and removed during use without damage to the surface to which it is adhered, additionally while maintaining adequate bond strength during use. Accordingly, the adhesive tab 14 can be secured to a surface, i.e. clothing, during use to prevent accidental projection of the withdrawal string 12 outside an article of clothing and to facilitate sanitary use and removal of the tampon, among other benefits.

As shown, the adhesive tab 14 is preferably positioned near the free end 19 of withdrawal string 12, away from the absorbent member 16. The further away from absorbent member 16 the adhesive tab 14 is, the further away a surface can be to which adhesive tab 14 is secured. As a result, the withdrawal string 12 can be secured to a surface that is at a further distance from the absorbent member 16.

Figure 2:
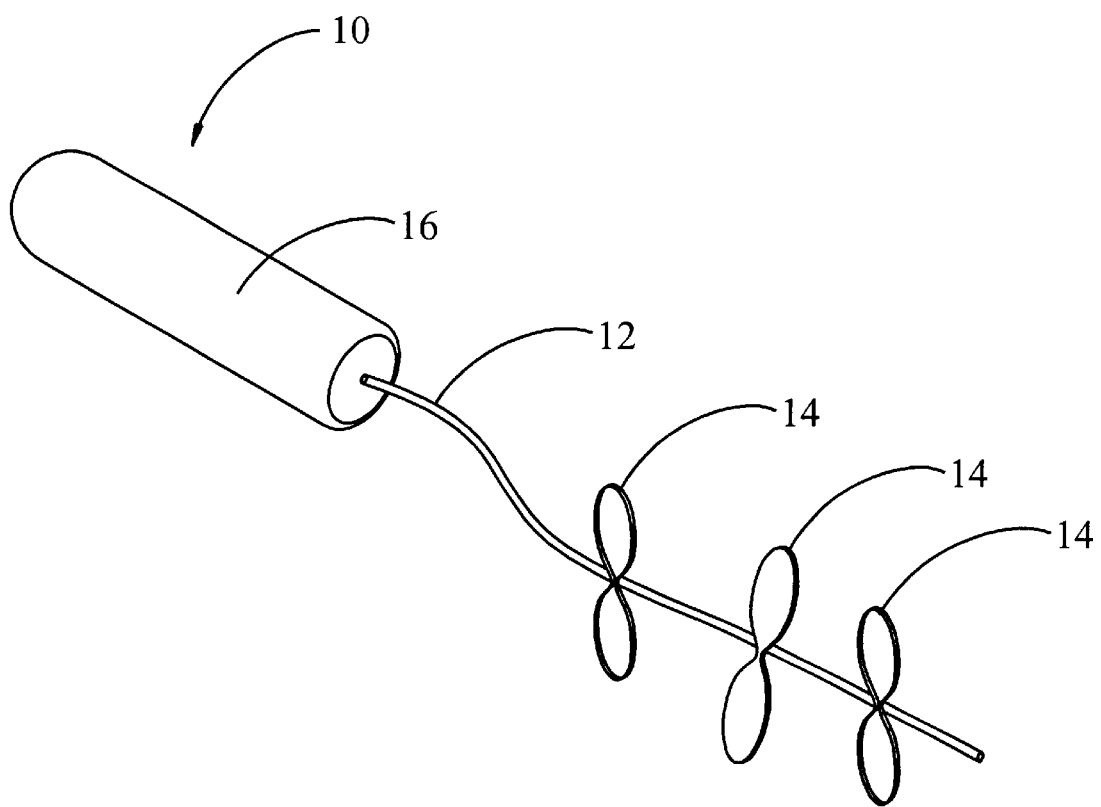
FIG. 2 is an orthogonal view of a plurality of adhesive tabs attached to a withdrawal string in accordance with the present invention.

Referring to FIG. 2, a plurality of adhesive tabs 14 may alternately be attached to withdrawal string 12 for adequate securement to a surface. As shown, three adhesive tabs 14 are attached to withdrawal string 12 at constant spacing, however, more or less adhesive tabs 14 may be attached, further at non-constant spacings. The number of adhesive tabs 14 and their particular spacing will vary according to the surface to which the adhesive tabs 14 are to be secured and the adhesive material that is applied to adhesive tabs 14. Moreover, the adhesive tabs 14 may be adjustable along the length of the withdrawal string 12 according to the preferences of the user.

Figure 3:
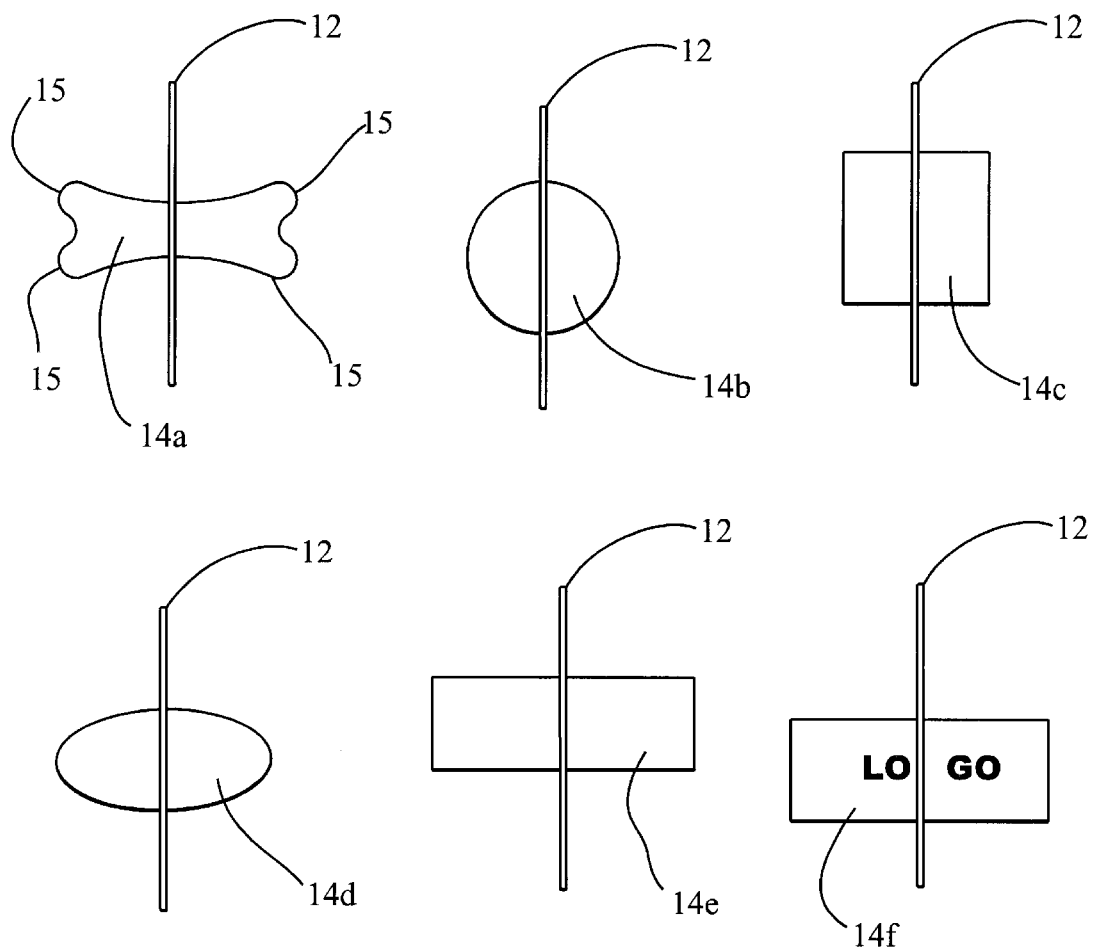
FIG. 3 is a plan view of example geometries for adhesive tabs in accordance with alternate embodiments of the present invention.

Referring now to FIG. 3, the geometrical configuration of adhesive tab 14 may be varied according to a variety of product design concerns including, but not limited to, manufacturability, cost, performance, marketing, and others. Accordingly, example geometrical configurations are shown that include shapes such as a bow 14a, a circle 14b, a square, 14c, an ellipse 14d, a rectangle, 14e, and a logo 14f. The logo 14f may be used to include the logo of a product manufacturer or other party as deemed appropriate for marketing or other purposes. Preferably, the geometrical configurations comprise rounded corners 15 as shown on the bow 14a configuration, to minimize any discomfort to the user should the adhesive tab 14 become dislodged during use. Clearly, a wide variety of geometrical configurations may be used for the adhesive tab 14, and accordingly, the examples shown in FIG. 3 should not be construed as limiting the invention to only those geometrical configurations shown.

Figure 4:
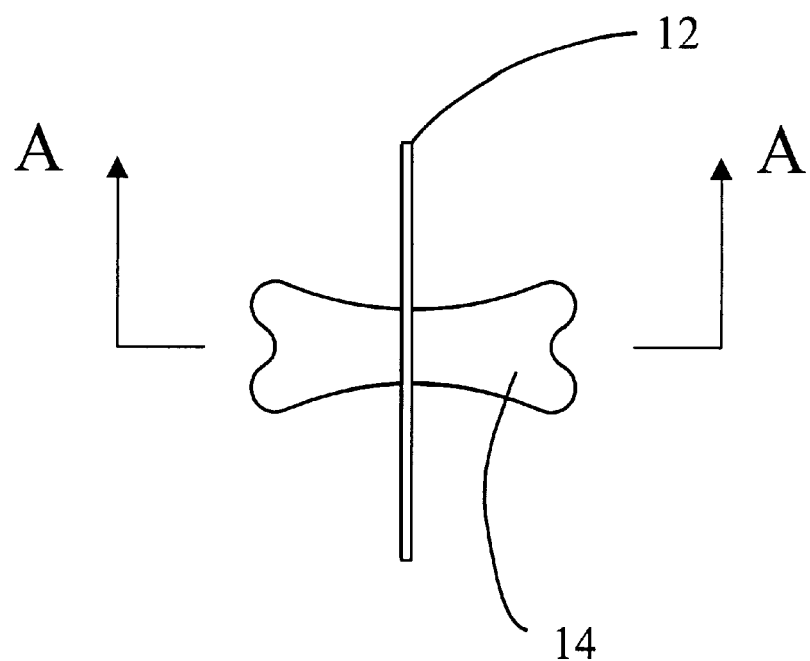
FIG. 4 is an enlarged orthogonal view of the interface between an adhesive tab and a withdrawal string in accordance with the present invention.
Figure 5:
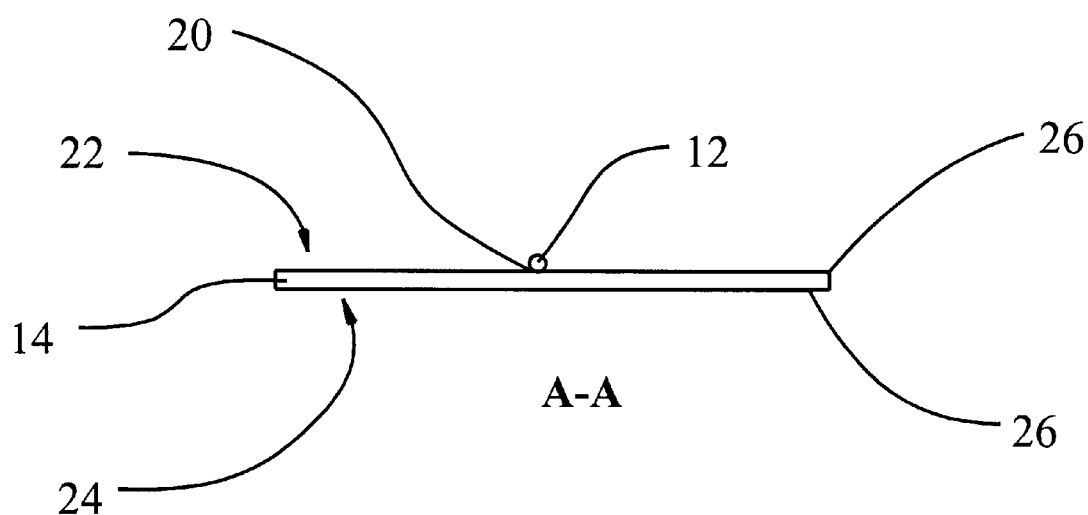
FIG. 5 is a sectional view, taken along line A—A of FIG. 4, of the interface between an adhesive tab and a withdrawal string in accordance with the present invention.

The interface between adhesive tab 14 and withdrawal string 12 for one embodiment of the present invention is illustrated with greater detail in FIGS. 4 and 5. As shown, the adhesive tab 14 is preferably secured to the withdrawal string 12 using an adhesive material 20. The adhesive material 20 is located at the interface between withdrawal string 12 and adhesive tab 14, wherein the adhesive material 20 provides a secure and permanent attachment for adhesive tab 14 to withdrawal string 12.

As further shown, adhesive tab 14 comprises a first side 22 and a second side 24. Preferably, first side 22 and second side 24 are coated with an adhesive layer 26, which has a low shear strength so that adhesive tab 14 can be easily secured and removed, repeatedly, as required by the user. Alternately, either first side 22 or second side 24 may be coated with the adhesive layer 26, rather than coating both sides. Moreover, adhesive layer 26 may be applied to all or a portion of either the first side 22 or the second side 24.

Figure 6:
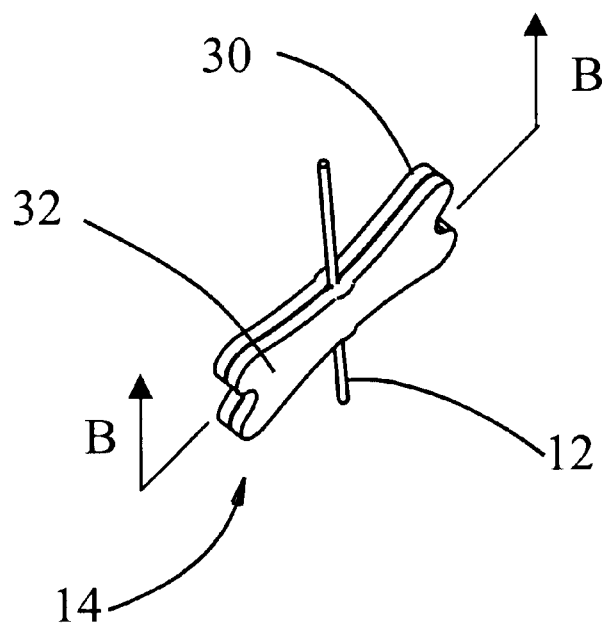
FIG. 6 is an enlarged orthogonal view of the interface between an adhesive tab and a withdrawal string in accordance with an alternate embodiment of the present invention.
Figure 7:
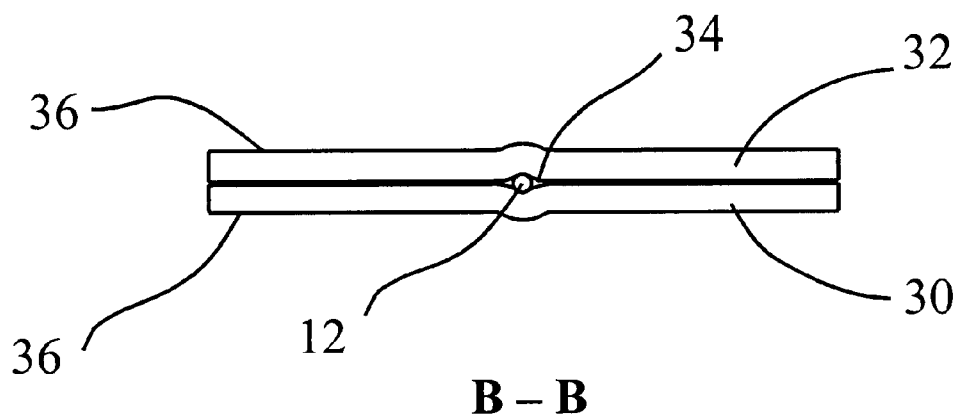
FIG. 7 is a sectional view, taken along line B—B of FIG. 6, of the interface between an adhesive tab and a withdrawal string in accordance with an alternate embodiment of the present invention.

Referring to FIGS. 6 and 7, an alternate embodiment for adhesive tab 14 is illustrated, wherein adhesive tab 14 comprises a first element 30 and a second element 32. As shown, withdrawal string 12 is attached to the adhesive tab 14 between first element 30 and second element 32 with an adhesive material 34. Additionally, the adhesive material 34 secures the first element 30 to the second element 32. As with the previous embodiment, first element 30 and second element 32 are coated with an adhesive layer 36, which has a low shear strength so that adhesive tab 14 can be easily secured and removed, repeatedly, as required by the user. In another preferred form, either first element 30 or second element 32 may be coated with the adhesive layer 36, rather than coating both elements. Additionally, adhesive layer 36 may be applied to all or a portion of the first element 30 or the second element 32.

Figure 8:
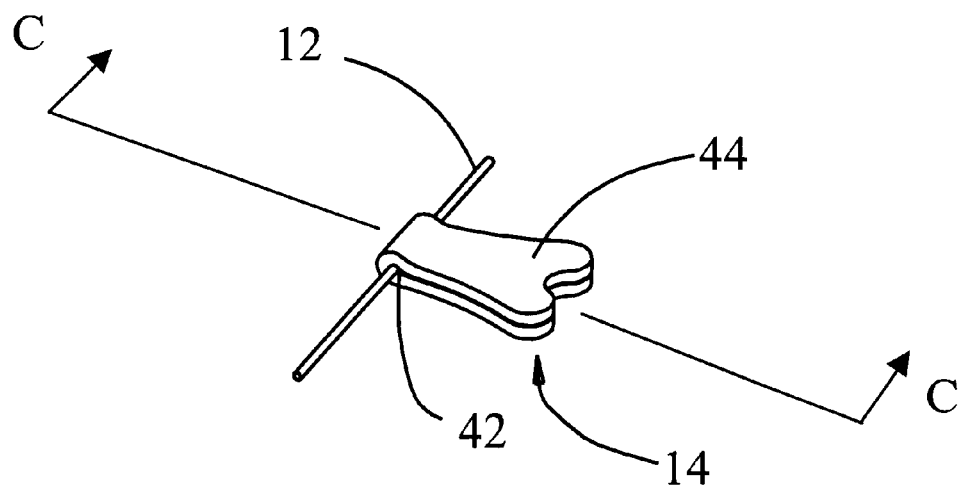
FIG. 8 is an enlarged orthogonal view of the interface between an adhesive tab and a withdrawal string in accordance with an alternate embodiment of the present invention.
Figure 9:
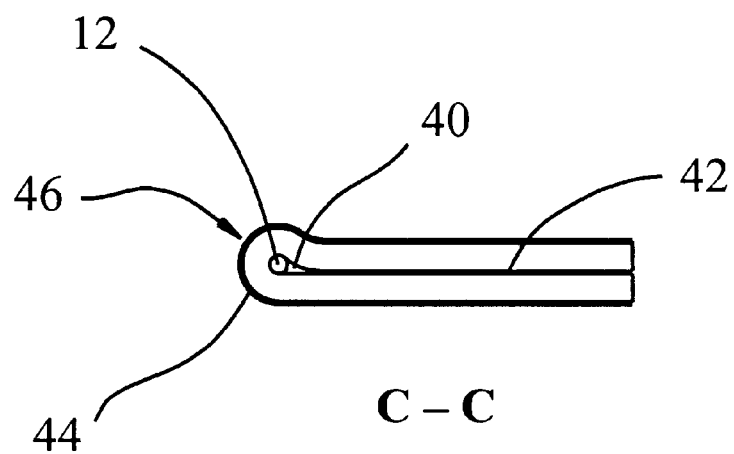
FIG. 9 is a sectional view, taken along line C—C of FIG. 8, of the interface between an adhesive tab and a withdrawal string in accordance with an alternate embodiment of the present invention.

Yet a further alternate embodiment for adhesive tab 14 is illustrated in FIGS. 8 and 9. As shown, adhesive tab 14 is wrapped around withdrawal string 12, wherein the withdrawal string 12 is attached to an inner side 42 of the adhesive tab 14 with an adhesive material 40. Additionally, the adhesive material 40 secures the inner side 42 of the adhesive tab 14 to itself, thereby leaving an outer side 44 exposed for securing the adhesive tab 14 to a surface. Accordingly, the outer side 44 is coated with an adhesive layer 46 that has a low shear strength so that adhesive tab 14 can be easily secured and removed, repeatedly, as required by the user. Further, adhesive layer 46 may be applied to all or a portion of the outer side 44.

Figure 10:
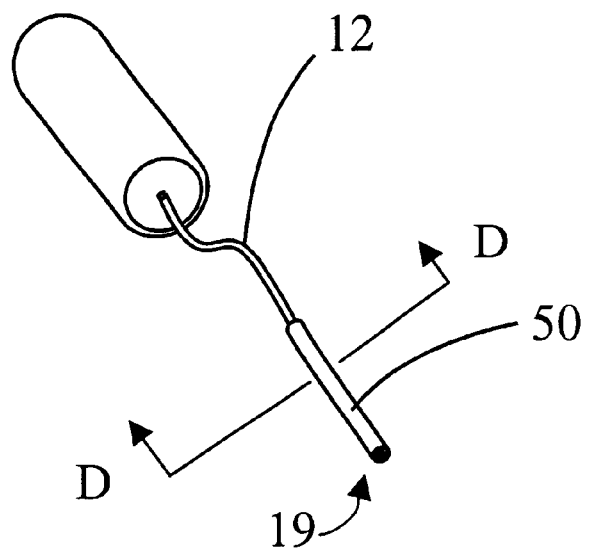
FIG. 10 is an orthogonal view of a withdrawal string having an adhesive coating in accordance with an alternate embodiment of the present invention.
Figure 11:
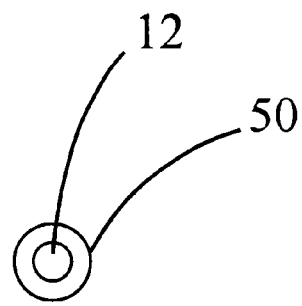
FIG. 11 is a sectional view, taken along line D—D of FIG. 10, of the adhesive coating applied to the surface of a withdrawal string in accordance with an alternate embodiment of the present invention.
Figure 12:
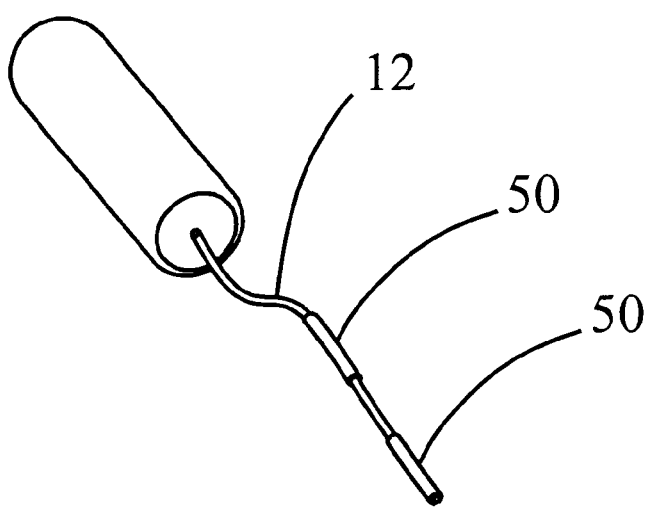
FIG. 12 is an orthogonal view of a withdrawal string having alternating segments of adhesive coating in accordance with an alternate embodiment of the present invention.

Referring now to FIGS. 10 and 11, another preferred form of the present invention is illustrated that comprises an adhesive coating 50 applied to at least a portion of the withdrawal string 12. Preferably, the adhesive coating 50 covers at least a portion of the withdrawal string 12 at the free end 19 thereof. Further, the adhesive coating 50 has a low shear strength so that the withdrawal string 12 can be easily secured and removed, repeatedly, as required by the user. Alternately, the adhesive coating 50 may be applied in segments as illustrated in FIG. 12, rather than as a continuous coating. Moreover, the adhesive coating 50 may be applied to all or a portion of withdrawal string 12 according to the particular bonding requirements.

Figure 13:
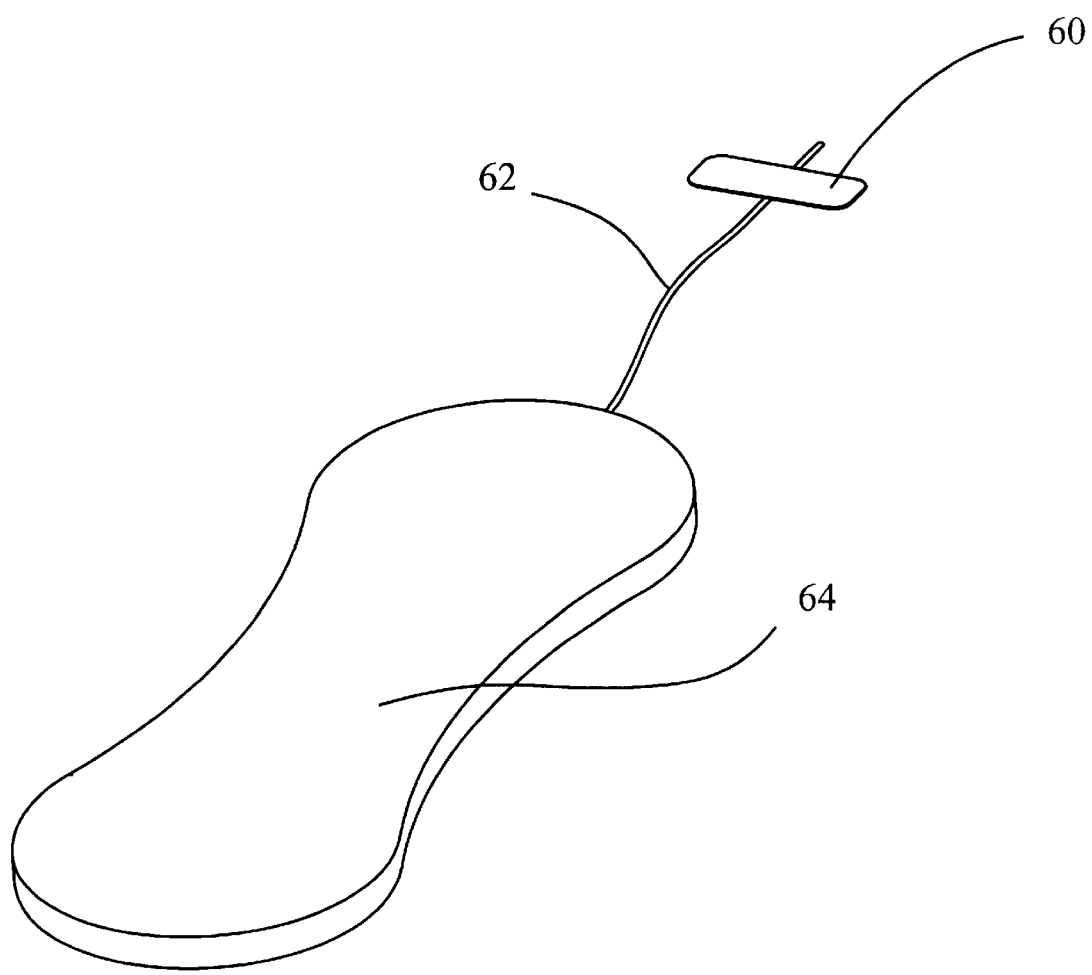
FIG. 13 is an orthogonal view of the adhesive element applied to a removal portion of a sanitary napkin in accordance with an alternate embodiment of the present invention.

Referring to FIG. 13, yet another preferred form of the present invention is illustrated that comprises an adhesive element 60 applied to a removal portion 62 of a sanitary napkin 64. The adhesive element 60 may be an adhesive tab or an adhesive coating as previously described, or other attachment device as commonly known in the art. Furthermore, the adhesive element 60 may be applied to a catamenial hygiene product that incorporates any such removal portion 62 or variations thereof.

Preferably, the adhesive layer that secures the adhesive tab 14 to a surface and the adhesive coating that secures the withdrawal string 12 to a surface is a microsphere type adhesive, wherein the adhesive adheres lightly and allows the adhesive tab 14 to be repositionable because the microspheres limit the amount of surface area contact between the adhesive tab 14 and the surface. Additionally, the adhesive material that attaches the withdrawal string 12 to the adhesive tab 14 is preferably an epoxy, or other adhesive commonly known in the art that is capable of properly securing the adhesive tab 14 to the withdrawal string 12 during use.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A system to secure the withdrawal string of a tampon to a surface, wherein the withdrawal string comprises an exterior surface and an adhesive coating applied to at least a portion the exterior surface in alternating segments along the portion of the withdrawal string such that when the withdrawal string is pressed against the surface, the adhesive coating secures the withdrawal string to the surface.

2. A catamenial device comprising:
    an absorbent member;
    a removal portion attached to the absorbent member; and
    an adhesive coating applied to at least a portion of the exterior surface of the removal portion in alternating segments such that when the removal portion is pressed against the surface, the adhesive coating secures the removal portion to the surface.

3. The device of claim 2, wherein the absorbent member is a tampon.

4. The device of claim 2, wherein the absorbent member is a sanitary napkin.

5. A system to secure a removal portion of an absorbent member of a catamenial hygiene product to a surface, the system comprising:
    an adhesive coating applied in alternating segments to the removal portion,
    wherein the adhesive coating secures the removal portion to the surface when pressed against the surface.

* * * * *